US007588602B2

(12) United States Patent
Ragbir

(10) Patent No.: US 7,588,602 B2
(45) Date of Patent: Sep. 15, 2009

(54) HIP PROSTHESIS

(75) Inventor: Shelia Ragbir, Whim (TT)

(73) Assignee: Mariasal Investment N.V., Willemstad, Curacao (AN)

( * ) Notice: Subject to any disclaimer, the term of this patent is extended or adjusted under 35 U.S.C. 154(b) by 186 days.

(21) Appl. No.: 10/547,126

(22) PCT Filed: Aug. 8, 2003

(86) PCT No.: PCT/IB03/03607

§ 371 (c)(1),
(2), (4) Date: Aug. 26, 2005

(87) PCT Pub. No.: WO2004/112659

PCT Pub. Date: Dec. 29, 2004

(65) Prior Publication Data

US 2006/0173550 A1    Aug. 3, 2006

(30) Foreign Application Priority Data

Jun. 20, 2003   (CH)   .................................... 1089/03

(51) Int. Cl.
*A61F 2/40* (2006.01)
(52) U.S. Cl. .................................................. 623/19.14
(58) Field of Classification Search .............. 623/22.42, 623/23.11–23.38, 23.52, 23.46
See application file for complete search history.

(56) References Cited

U.S. PATENT DOCUMENTS

| 2,223,871 | A | * | 12/1940 | Johnson | ....................... 411/453 |
| 3,918,441 | A |   | 11/1975 | Getscher | |
| 5,476,345 | A | * | 12/1995 | Papadopoulos | ............. 405/272 |
| 5,902,340 | A |   | 5/1999 | Enzerink et al. | |
| 5,935,172 | A | * | 8/1999 | Ochoa et al. | ............. 623/23.36 |
| 7,189,261 | B2 | * | 3/2007 | Dews et al. | ............. 623/19.14 |
| 2001/0049561 | A1 | * | 12/2001 | Dews et al. | ............. 623/19.14 |

FOREIGN PATENT DOCUMENTS

| EP | 0 000 549 | 2/1979 |
| EP | 0 677 281 | 10/1995 |
| IT | 0677281 A2 * | 3/1995 |

* cited by examiner

*Primary Examiner*—Corrine McDermott
*Assistant Examiner*—Ann Schillinger
(74) *Attorney, Agent, or Firm*—Young & Thompson

(57) ABSTRACT

Hip prosthesis structure includes a stem to be inserted into the upper portion of the femur, this stem having in its top a cavity for housing the free end of a shaped neck which carries on its other end a spherical head to be joined to the acetabulum of the hip. The free end of the neck is shaped in the form of two half truncated cones positioned so that they are mirror images of each other and delimited transversely by two bases which are essentially flat and parallel. The half truncated cones are linked to each other by two surfaces which form two recesses inside the planes tangent to the two half truncated cones on opposite sides of the plane which contains their axes, the shape of the cavity being complementary to the solid formed by the two half truncated cones and by the two planes tangent to them.

2 Claims, 1 Drawing Sheet

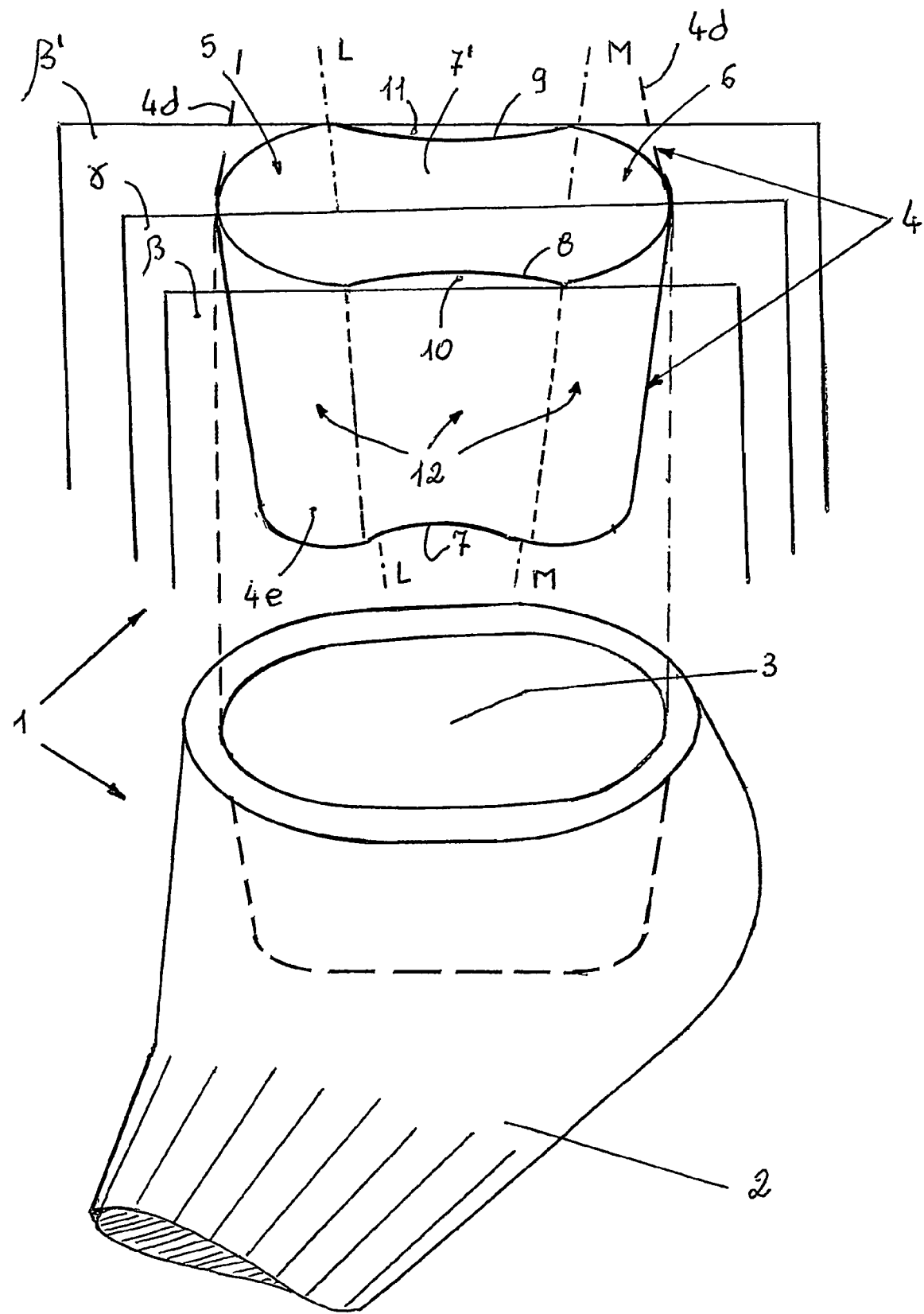

HIP PROSTHESIS

FIELD OF THE INVENTION

The present invention relates to the field of prostheses used in orthopaedic surgery.

BACKGROUND OF THE INVENTION

More specifically, the invention relates to a hip prosthesis structure. As is known to persons skilled in the art, this structure essentially comprises a stem which is to be inserted into the upper portion of the femur and which has a cavity in its top for the stable housing of the free end of a shaped bar, called the "neck", on the other end of which is fitted a spherical head which is joined to the acetabulum of the hip of the patient on whom the operation is performed.

Clearly, the stability of the joint between the neck of the prosthesis and the said cavity of the stem in which it is inserted is of fundamental importance to the success of the operation: this is because relative movements between the two parts after the fitting of the prosthesis can generate debris which may lead to inflammation, degeneration and fracture of the tissues of the various parts of the hip region, with unforeseeable consequences which may seriously compromise the success of the operation.

To prevent the movements in question, the free end of the said neck and the said cavity are at present constructed with complementary profiles and, in order to improve the reliability of the joint, they are made in the form of a solid consisting of two bases, essentially parallel to each other, linked by surfaces inclined with respect to the said bases and converging towards the stem.

This forms a joint which is slightly forced between inclined planes which should ensure the maximum stability of the parts by preventing relative movements between them.

However, although attempts are made to machine the neck and the corresponding cavity in the most precise way, it is impossible in practice to obtain perfect complementarity of the parts, and in almost all cases a correct joint is made between the opposing inclined surfaces perpendicular to only one of the two orthogonal planes of symmetry.

Specialists in the field know that the stresses acting on a hip prosthesis reach very high levels in response to moments applied on a vertical plane perpendicular to the plane passing through both hip joints, whereas they are much smaller for moments applied on the latter plane.

Consequently, if the joint between the neck and cavity permits larger movements in the direction of the aforesaid stresses, the previously mentioned problems arise and can adversely affect the results of an operation. Since it is impossible to know for certain in which direction the joint is correct and in which direction it is defective, there is a 50% probability that problems will arise after operations with the present hip prostheses.

In view of the above, the inventor of the hip prosthesis structure described herein considers that the risks of post-operative complications can be reduced considerably by making the said neck and the said cavity in such a way as to provide certainty of the absolute correctness of their joining in the direction described previously in which the maximum stresses occur, while deliberately forgoing any attempt to achieve a simultaneous forced joint between the parts in the direction perpendicular to the said direction, in which negligible risks are incurred.

SUMMARY OF THE INVENTION

For this purpose, the inventor has devised a hip prosthesis structure in which the said free end of the neck is shaped in the form of two half truncated cones positioned so that they are mirror images of each other and delimited transversely by two bases which are essentially flat and parallel, the two half truncated cones being linked to each other by two surfaces which form two slight recesses which are inside the two planes tangent to the half truncated cones on opposite sides of the plane containing their axes.

The shape of the said cavity is complementary to the solid formed by the two half truncated cones and by the two planes tangent to them.

Thus the tightness of the joint is achieved solely by means of the two half truncated cones. The desired result is achieved by positioning these in such a way that this tightness opposes the greater stresses, while the remaining parts of the profiles of the neck and cavity are simply positioned close to each other.

BRIEF DESCRIPTION OF THE DRAWING

A preferred embodiment of the invention will now be described with reference to the attached FIGURE, which shows an exploded and partially transparent view of the free end of a neck (the other end 4d to which a spherical head is fitted is not illustrated, but simply indicated in broken lines) and of a stem with a cavity made according to the invention.

DETAILED DESCRIPTION OF THE INVENTION

The FIGURE shows how, in a hip prosthesis structure 1 according to the invention, the terminal part of the said neck 4 has, as stated above, the shape of two half truncated cones 5 and 6, positioned so that they are mirror images of each other and delimited transversely by two bases 7 and 7' which are essentially flat and parallel. The said two half truncated cones 5 and 6 are linked to each other by two surfaces 8 and 9 which form two slight recesses 10 and 11 (emphasized for clarity in the drawing) which are inside the planes $\beta$ and $\beta'$ tangent to the half truncated cones 5 and 6 on opposite sides of the plane Y containing their axes L-L and M-M. The shape of the said cavity 3 of the stem 2 is complementary to the solid 12 formed by the two half truncated cones 5 and 6 and by the said two planes $\beta$ and $\beta'$ tangent to them.

This achieves the desired result, in other words a tightness of the joint which is certain only at the positions of the two half truncated cones 5 and 6, in other words in the direction in which the higher and therefore more dangerous stresses occur.

It should be noted that the aforesaid recesses 10 and 11 are in reality very slight depressions, sufficient only to prevent the possibility of interference with the inner parts of the cavity facing them.

I claim:

1. Hip prosthesis structure (1) comprising in combination a stem (2) to be inserted into the upper portion of the femur, and a shaped bar or neck, said stem (2) having in its top a cavity (3) in which is disposed a free end (4e) of said shaped bar or neck (4), said shaped bar or neck carrying on another end (4d) a spherical head to be joined to the acetabulum of the hip, characterized in that said free end (4e) of said neck (4) is shaped in the form of two half truncated cones (5 and 6) having conical axes (L-L, M-M) transversely spaced from each other on opposite sides of a longitudinally extending plane ($\gamma$) and positioned so that said cones are mirror images of each other; and each truncated cone being delimited transversely by two bases (7 and 7') which are essentially flat and parallel, the half truncated cones being linked to each other by two transversely oriented surfaces (8 and 9) which form two recesses (10 and 11) inside planes ($\beta$) and ($\beta'$) tangent to said two half truncated cones (5 and 6), the shape of said cavity (3) being complementary to said free end of said shaped bar or neck formed by said two half truncated cones (5 and 6) and by said planes ($\beta$) and ($\beta'$) tangent to said cones.

2. A prosthesis structure as claimed in claim 1, there being only one said recess on each side of said structure.

\* \* \* \* \*